United States Patent [19]
Lam et al.

[11] Patent Number: 6,096,695
[45] Date of Patent: *Aug. 1, 2000

[54] SULFURIZED PHENOLIC ANTIOXIDANT COMPOSITION, METHOD OF PREPARING SAME, AND PETROLEUM PRODUCTS CONTAINING SAME

[75] Inventors: William Y. Lam, Glen Allen; Vincent J. Gatto, Midlothian, both of Va.

[73] Assignee: Ethyl Corporation, Richmond, Va.

[ * ] Notice: This patent is subject to a terminal disclaimer.

[21] Appl. No.: 08/657,141

[22] Filed: Jun. 3, 1996

[51] Int. Cl.$^7$ .................................................. C01M 135/30
[52] U.S. Cl. .................. 508/570; 508/572; 508/573; 44/435; 252/404; 252/406
[58] Field of Search ..................... 508/570, 572, 508/573; 44/435; 252/404, 406

[56] References Cited

U.S. PATENT DOCUMENTS

| | | | |
|---|---|---|---|
| 3,250,712 | 5/1966 | Coffield | 252/48.2 |
| 3,410,798 | 11/1968 | Cohen | 252/37.2 |
| 3,678,115 | 7/1972 | Fujisawa et al. | 260/609 F |
| 3,718,699 | 2/1973 | Fujisawa et al. | 260/608 |
| 3,835,196 | 9/1974 | Fujisawa et al. | 260/608 |
| 3,929,654 | 12/1975 | Brewster et al. | 252/48.2 |
| 4,551,259 | 11/1985 | Braid | 508/571 |
| 4,740,578 | 4/1988 | Onoe et al. | 568/62 |
| 4,877,902 | 10/1989 | Gatto | 568/23 |
| 4,946,610 | 8/1990 | Lam et al. | 252/48.2 |
| 5,004,481 | 4/1991 | Lam et al. | 44/435 |
| 5,045,089 | 9/1991 | Lam et al. | 44/435 |
| 5,166,439 | 11/1992 | Lam et al. | 564/384 |
| 5,319,144 | 6/1994 | Chiu | 568/23 |
| 5,376,290 | 12/1994 | Meier et al. | 252/47.5 |
| 5,427,701 | 6/1995 | Meier et al. | 252/47.5 |
| 5,516,441 | 5/1996 | Denis | 508/571 |

FOREIGN PATENT DOCUMENTS 1290132  9/1972  United Kingdom .

OTHER PUBLICATIONS

Synthesis, Nov., 1972, pp. 624–625.
Synthesis, Jan., 1973, pp. 38–39.
T. Fujisawa, et al.: "The sulphurisation of sterically hindered phenols with sulphur. A convenient synthesis of 4, 4'–thio–bis–(2, 6–dialkylphenols) and 2, 6–dialkyl–4–mercaptophenols" Synthesis, No. 1, Jan. '73, Stuttgart, DE, pp. 38–39, XP002071197.
A.J. Neale, et al.: "Some observations of the reactions between phenol and sulphur" Tetrahedron, vol. 25, No. 18, Sep. '69, Oxford, GB, pp. 4593–4597, XP000569375.

*Primary Examiner*—Jacqueline V. Howard
*Attorney, Agent, or Firm*—Dennis H. Rainear; Thomas Hamilton

[57] ABSTRACT

The present invention relates generally to substantially liquid, chlorine-free, sulfur-bridged phenols useful as antioxidants and more specifically to the preparation of a substantially liquid, chlorine-free, sulfur-bridged, hindered phenol compositions which are effective antioxidant(s) in lubricating oils without causing excessive copper corrosion. The invention also includes lubricating oils containing an antioxidant additive of the present invention, as well as a method of reducing oxidation in the lubricating oil used in a machine such as an internal combustion engine.

16 Claims, No Drawings

SULFURIZED PHENOLIC ANTIOXIDANT COMPOSITION, METHOD OF PREPARING SAME, AND PETROLEUM PRODUCTS CONTAINING SAME

TECHNICAL FIELD

The present invention is in the field of lubricating oils used primarily in passenger cars and trucks.

BACKGROUND

In providing lubricants for internal combustion engines, such as those used in passenger cars and trucks, it is desirable to provide antioxidant additives that reduce engine corrosion.

Antioxidants in the form of hindered, sulfur-bridged phenols having a branched alkyl group on the alpha carbon atom and made by reacting the phenol with sulfur dichloride in a solvent with recovery of a crystalline product from the reaction mixture is disclosed in U.S. Pat. No. 3,250,712.

The preparation of a crystalline 4,4-thiobis-(2,6-di-t-butylphenol) product by reacting the phenol with a sulfur halide in a solvent such as acetonitrile, carbon disulfide or carbon tetrachloride with or without a catalyst followed by treating the reaction mixture with alkali hydroxide in alcohol is disclosed in U.S. Pat. No. 3,678,115.

The preparation of a liquid lubricant oil additive mixture of 45–75 wt % orthoalkylphenol and certain amounts of mono-, di-, tri- and tetrasulfides of the phenol by the reaction of an excess of the phenol with sulfur using an organic amine catalyst is disclosed in U.S. Pat. No. 3,929,654. It is also reported in this patent that sulfurized alkylphenols prepared by reacting an alkylphenol with sulfur mono- or dichloride tend to cause copper corrosion probably due to the presence of corrosive sulfur species such as sulphochlorinated alkylphenol.

U.S. Pat. No. 4,946,610 discloses a liquid, sulfur-bridged, hindered phenol antioxidant composition that is prepared by reacting a mixture of hindered phenols with a sulfur chloride in the presence of a polar modifier. The composition is an effective antioxidant in lubricating oils without causing excessive copper corrosion.

One of the objects of this invention is the preparation of an oil soluble, chlorine-free, sulfurized hindered phenolic antioxidant that does not cause excessive copper corrosion and is a highly effective antioxidant in low phosphorus (<1000 ppm phosphorus) lubricating oils used primarily in passenger cars and trucks.

SUMMARY OF THE INVENTION

This invention relates generally to substantially liquid, chlorine-free, sulfur-bridged phenols useful as antioxidants and more specifically to the preparation of a substantially liquid, chlorine-free, sulfur-bridged, hindered phenol compositions which are effective antioxidant(s) in lubricating oils without causing excessive copper corrosion. The invention also includes lubricating oils containing an antioxidant additive of the present invention, as well as a method of reducing oxidation in the lubricating oil used in a machine such as an internal combustion engine.

As used herein, reference to substantially liquid character refers to compositions that are chiefly liquid. In this regard, aged samples of substantially liquid, chlorine-free, sulfur-bridged phenols of the present do tend to form a slight amount of crystallization, generally around the sides of a container where product comes in contact with air and the glass container surface. Sometimes more substantial crystallization is seen as a slight sediment at the bottom of the sample. Generally the amount of crystallization is small but changes significantly with a small drop in sulfur content. For example, material prepared with 3.2 moles sulfur/mole active phenol generally has only slight crystallization from aged samples at room temperature. However, a drop in sulfur content to 2.9 moles sulfur/mole active phenol gives significantly more crystallization. For example, 50 Wt % oil blends stored at 50–60° C. are completely liquid. This is still an advantage over the pure compounds that have melting points over 100 degrees C. A higher sulfur content should improve liquidity but would significantly hurt copper corrosion characteristics. Example VI below illustrates this in more detail.

In general terms, the antioxidant compositions of the present invention include antioxidant compositions comprising at least one thiobisphenol according to the formulae selected from the group consisting of:

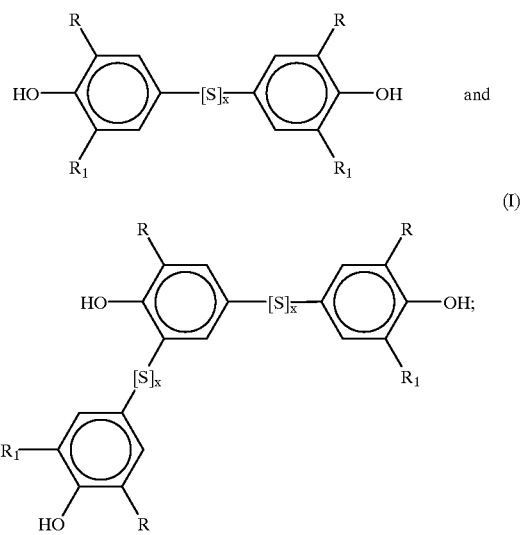

wherein R is selected from the group consisting of alkyl groups and hydrogen, wherein $R_1$ is selected from the group consisting of alkyl groups and hydrogen, and wherein X is in the range of from 1 to 6; and wherein the antioxidant composition is substantially free of chlorine, and wherein the antioxidant composition being in a substantially liquid form.

In broadest terms the invention includes sulfur-bridged phenols referred to as thiobisphenols prepared in accordance with the general synthetic scheme:

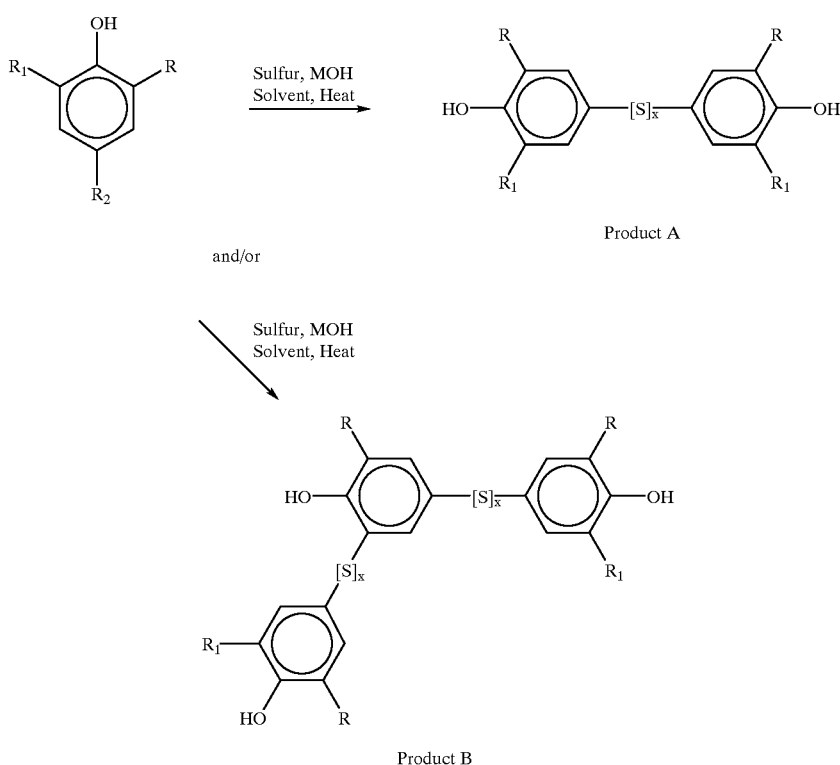

Product A and/or

Product B wherein R is selected from the group consisting of alkyl groups and hydrogen, $R_1$ is selected from the group consisting of alkyl groups and hydrogen, $R_2$ is selected from the group consisting of alkyl groups and hydrogen, and X is in the range of from 1 to 6. M may be selected from lithium, sodium, potassium, and cesium.

Byproducts may include several species such as those depicted here:

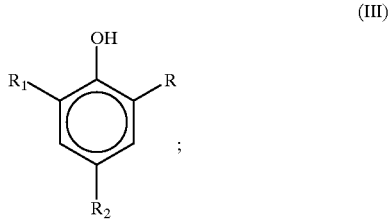

wherein in species C, R=alkyl, R1 and R2=H; in species D, R=alkyl, R1=alkyl, R2=H; in species E, R=alkyl, R1 and R2=alkyl.

The main advantage of this invention over that described in U.S. Pat. No. 4,946,610 is the use of a chlorine-free sulfur source and the preparation of a product with a higher sulfur content and less unreacted 2,6-dialkylphenol. A further advantage is that the sulfurized hindered phenol product is substantially chlorine-free.

The present invention also includes lubricating compositions and liquid organic fuels containing an additive according to the present invention.

It is preferred that the additive be present at a concentration in the range of from 0.05% to about 5.0% by weight, and most preferably at a concentration in the range of from 0.5% to about 2.0% by weight.

The lubricating composition and liquid organic fuel of the present invention may additionally comprise at least one composition selected from the group consisting of dispersants, detergents, antiwear additives, supplemental antioxidants, viscosity index improvers, pour point depressants, corrosion inhibitors, rust inhibitors, foam inhibitors, and supplemental friction modifiers, as appropriate to the desired application and as is appreciated in the art. The supplemental antioxidants may include those selected from the group consisting of diphenylamines, alkylated diphenylamines, phenyl-napthylamines, tert-butylphenols, sulfurized alkylphenols, sulfurized olefins, dithiocarbamates, oil soluble copper compounds, and oil soluble molybdenum compounds. It is presently believed that the use of supplemental antioxidants will become more common in the future. Thus, it is preferred compositions of the present invention include more than one antioxidant in addition to sulfurized hindered phenols of the present invention.

Such lubricating compositions and liquid organic fuels may be formulated in accordance with practices known in the art using the additive of the present invention.

The present invention also includes a method of reducing the oxidative environment in a petroleum composition selected from the group consisting of lubricating compositions and organic fuels, which method comprising generally adding to the petroleum composition an effective amount of an antioxidant composition according to the present invention. Typically, an effective amount of the antioxidant composition will be in the ranges given herein.

The present invention also includes a method of producing a substantially liquid sulfurized hindered phenol, said method comprising the steps: (a) preparing a mixture of: (i) at least one substantially chlorine-free hindered phenol; (ii)

a substantially chlorine-free sulfur source; and (iii) at least one alkali metal hydroxide promoter; in a polar solvent; and (b) causing components (i), (ii) and (iii) to react for sufficient time and at sufficient temperature so as to form at least one chlorine-free sulfurized hindered phenol.

The hindered phenol may be selected from the group consisting of:

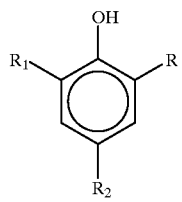

wherein R is selected from the group consisting of alkyl groups and hydrogen, $R_1$ is selected from the group consisting of alkyl groups and hydrogen, and $R_2$ is selected from the group consisting of alkyl groups and hydrogen. It is preferred that the R group and the $R_1$ group be selected from the group consisting of alkyl groups of 3 to 12 carbons and hydrogen, and most preferably from the group consisting of alkyl groups of 4 to 6 carbons and hydrogen.

The hindered phenol may be selected from the group consisting of: 2-t-butylphenol, 2,6-di-t-butylphenol, 2,4-di-t-butylphenol, 2-sec-butylphenol, 2,6-di-sec-butylphenol, 2,4-di-sec-butylphenol, 2-isopropylphenol, 2,6-diisopropylphenol, 2,4-diisopropylphenol, 2-t-octylphenol, 2,6-di-t-octylphenol, 2,4-di-t-octylphenol, 2-cyclopentylphenol, 2,6-dicyclopentylphenol, 2,4-dicyclopentylphenol, 2-t-butyl-p-cresol, 2,6-di-t-amylphenol, 2,4-di-t-amylphenol, 6-t-butyl-o-cresol 2,6-di-t-dodecylphenol, 2,4-di-t-dodecylphenol, 2-sec-butyl-p-cresol 2,6-di-t-octylphenol, 2,4-di-t-octylphenol, 6-sec-butyl-o-cresol, 2-t-octyl-p-cresol, 2-t-dodecyl-p-cresol, 2-t-butyl-6-isopropylphenol, 6-t-octyl-o-cresol, 6-t-dodecyl-o-cresol, and mixtures thereof, and most preferably will be selected from any two or more such hindered phenols.

It is preferred that the sulfur source comprise elemental sulfur.

The polar solvents used in accordance with the method of the present invention may be any appropriate polar solvent, such as those selected from the group consisting of 2-propanol, methanol, ethanol, 2-butanol, 1-butanol, t-butyl alcohol, 1-pentanol, 1-hexanol and 2-ethylhexanol; and preferably 2-propanol.

The chlorine-free sulfurized hindered phenols of the present invention may be prepared by reacting a hindered phenol mixture with elemental sulfur in the presence of an alkali metal hydroxide promoter and a polar solvent. The reaction may be carried out at the reflux temperature of the solvent. The process produces alkali metal sulfide waste that may be separated from the product by washing with water. Separation of the aqueous and organic phases may be facilitated by the addition of a non-polar solvent. After the water washes the non-polar solvent may be removed, yielding the substantially liquid sulfurized hindered phenol product.

The advantages of this process are that the sulfur source is substantially chlorine-free thus producing a chlorine-free sulfurized product. Use of a chlorine-free sulfur source also allows one to drive the reaction further to completion, i.e., reacting greater quantities of hindered phenol, while maintaining a low level of corrosion. It will be understood that reference to the product being substantially chlorine-free is intended to mean that the product is free of amounts of chlorine, in whatever oxidation state, that would cause copper corrosion in a given desired application.

The process thus described produces a composition that is highly sulfurized (typically greater than 8 wt. % sulfur in the final product), the main products being sulfur bridged 2,6-dialkylphenols. The number of bridging sulfur atoms between any two bridged phenolic rings can vary from 1 to 8. The process as described produces mostly bridges ranging from one to four sulfurs. Very small quantities of longer chained sulfur bridges, e.g. five, six, and seven, may be produced. Because chlorine-free products are produced, the reaction may be driven further to completion. Thus, products with low levels of unreacted hindered phenols can be made. An advantage of greater conversions in these reactions is that the products produced are less volatile, a property of practical importance in high temperature lubricant applications.

Another advantage of the process and product of the present invention is that the products are rendered in substantially liquid form which greatly enhances their solubility as an additive, such as when placed in a base oil.

It has also been found that the chlorine-free sulfurized hindered phenol product is an effective antioxidant in both conventional passenger car motor oils, i.e. oils containing approximately 1000 ppm phosphorus derived from ZDDP anti-wear additives, and low phosphorus passenger car motor oils, e.g. oils containing approximately 800 ppm phosphorus derived from ZDDP anti-wear additives.

DETAILED DESCRIPTION OF THE PREFERRED EMBODIMENT

In accordance with the foregoing summary the following presents a description of the preferred embodiments of the invention, presently considered to be the best mode thereof.

The process described in this invention produces a sulfurized hindered phenol product that has a number of advantages over sulfurized hindered phenols produced using different processes. First, the product produced is substantially liquid with very high solubility in oil. Second, the product is substantially chlorine-free and does not cause excessive copper corrosion. Third, the product is a highly effective antioxidant in both conventional motor oils and low phosphorus motor oils.

The process for producing this chlorine-free sulfurized hindered phenol involves reacting a hindered phenol mixture with elemental sulfur in the presence of an alkali metal hydroxide promoter and a polar solvent.

The hindered phenolic mixture used in this process should contain at least two different hindered phenols each having at least one hydrogen in the ortho or para position. Hindered phenols of this type are called reactive hindered phenols since at least one ortho or para hydrogen is available in the molecule for reaction with sulfur. By hindered phenol is meant that the phenol is substituted in at least one ortho position with branched chain C3 to C12 alkyl groups and preferably a C4 to C6 alkyl group. Examples of suitable ortho-alkylphenols include:

| 2-t-butylphenol | 2,6-di-t-butylphenol | 2,4-di-t-butylphenol |
|---|---|---|
| 2-sec-butylphenol | 2,6-di-sec-butylphenol | 2,4-di-sec-butylphenol |
| 2-isopropylphenol | 2,6-diisopropylphenol | 2,4-diisopropylphenol |
| 2-t-octylphenol | 2,6-di-t-octylphenol | 2,4-di-t-octylphenol |
| 2-cyclopentylphenol | 2,6-dicyclopentylphenol | 2,4-cyclopentylphenol |
| 2-t-butyl-p-cresol | 2,6-di-t-amylphenol | 2,4-di-t-amylphenol |
| 6-t-butyl-o-cresol | 2,6-di-t-dodecylphenol | 2,4-di-t-dodecylphenol |
| 2-sec-butyl-p-cresol | 2,6-di-t-octylphenol | 2,4-di-t-octylphenol |
| 6-sec-butyl-o-cresol | 2-t-octyl-p-cresol | 2-t-dodecyl-p-cresol |
| 2-t-butyl-6-isopropylphenol | 6-t-octyl-o-cresol | 6-t-dodecyl-o-cresol |

Non-reactive hindered phenols may also be present in the hindered phenol mixture. By non-reactive is meant a hindered phenol with no available hydrogens in the ortho or para positions of the phenol. These phenols are completely substituted at the reactive sites of the phenol aromatic ring and are thus not suitable for reaction with sulfur. Examples of such non-reactive hindered phenols include:

| | | |
|---|---|---|
| 2,4,6-tri-t-butylphenol | 4,6-di-t-butyl-o-cresol | 2,6-di-t-butyl-p-cresol |
| 2,4,6-tri-sec-butylphenol | 4,6-di-sec-butyl-o-cresol | 2,6-di-sec-butyl-p-cresol |
| 2,4,6-tri-isopropylphenol | 4,6-diisopropyl-o-cresol | 2,6-diisopropyl-p-cresol |
| 2,4,6-tri-t-amylphenol | 2,4,64-tri-t-octylphenol | 2-t-butyl-6-sec-butyl-p-cresol |

Suitable hindered phenol mixtures contain 75 wt. % to 95 wt. % of a reactive hindered phenolic mixture containing two or more reactive hindered phenols, and from 5 wt. % to 25 wt. % of a non-reactive hindered phenolic mixture containing one or more non-reactive hindered phenols. The mixture preferably contains at least 50 weight % to 75 weight % of a di-ortho branched chain alkylphenol such as 2,6-di-t-butylphenol. An example of a specific hindered phenolic mixture used in this invention contains 75 wt. % 2,6-di-t-butylphenol and 10 wt. % 2-t-butylphenol as the reactive hindered phenol component, and 13 wt. % 2,4,6-tri-t-butylphenol as the non-reactive hindered phenolic component.

The hindered phenol mixture may be reacted with elemental sulfur in amounts based on the total reactive hindered phenolic content. Typically, a total of 2.8 to 3.6 moles of elemental sulfur are used per mole of reactive hindered phenols. Lower levels of sulfur produce less sulfur bridged hindered phenols and/or substantially solid products while higher levels of sulfur produce a more corrosive product. The physical form of the elemental sulfur is not critical.

The alkali metal hydroxide used to promote the reaction may be any of the commercial alkali metal hydroxides, e.g. sodium hydroxide, potassium hydroxide, lithium hydroxide, cesium hydroxide. The amount of alkali metal hydroxide used typically is based on the total amount of active hydrogens in the reactive hindered phenolic mixture. A total of 1.0 moles of alkali metal hydroxide preferably are used for every mole of active hydrogens derived from the reactive hindered phenols. For the hindered phenolic mixture described above the alkali metal hydroxide content is determined as follows:

The order or rate of addition of the reagents is not critical, and the reaction time and temperature may be varied. After the reaction period the solvent is removed by distillation. Vacuum may be applied in order to facilitate the removal of the last fractions of solvent. The concentrated reaction mixture contains substantial amounts of various alkali metal sulfide salts that may be removed from the product by water washes. Generally, two to three water washes are sufficient to remove the salts with the last water wash containing a small amount of acid. A non-polar solvent may be added during the water washes to facilitate the separation of the organic product from the water phase. Examples of non-polar solvents that may be used include hexane, petroleum ether, ethyl ether, chloroform, methylene chloride, toluene, xylene, benzene, pentane, heptane, and octane. After the last aqueous wash the phases are separated and the organic mixture is concentrated by distillation to give the desired sulfurized hindered phenol product. The reaction is illustrated in FIG. II.

The sulfurized liquid hindered phenol product includes, depending upon the phenols in the initial mixture, mixtures of sulfur bridged bisphenols and/or polyphenol compounds such as are represented by Products A and B in the above reaction scheme, where $[S]_x=1$ to 6, R is C3 to C12 branched alkyl and R1 and R2 are independently hydrogen or C3 to C12 branched alkyl. The product also contains 10 to 25 percent of unreacted phenols which contain an ortho or para hydrogen (species C and D in FIG. III). Of course, the non-reactive hindered phenols originally present in the starting material are unchanged in the reaction and remain in the product (species E in FIG. III).

The sulfurized hindered phenol product typically will be isolated as a high viscosity oil. The product can be used as is or may be diluted in a process or lubricating oil. Typical dilutions contain between 30 wt. % and 95 wt. % of the hindered sulfurized phenolic product with the remainder being one or more mineral or synthetic based lubricants. Typically, dilution is required to facilitate blending in regions were temperatures are low, e.g. arctic regions.

The sulfurized hindered phenol products are added to lubricating compositions or liquid organic fuels in concentrations ranging from 0.05 to 5.0 wt. %, and preferably from 0.5 to 2.0 wt. %. Typically, the product is added to the oil or fuel in the form of an additive package concentrate. The amount of product in the concentrates generally varies from 0.5 to 50 weight percent or more. The concentrates may also contain other additives.

In crankcase oil applications the product composition can vary significantly based on the customer and specific appli-

| | | |
|---|---|---|
| 2,6-di-t-butylphenol | 75 g/206.36 g/mole = 0.363 moles 1 active H | 0.363 mole H |
| 2-t-butylphenol | 9 g/150.2 g/mole = 0.060 moles 2 active H | 0.120 mole H |
| Total Reactive Phenol | 84 g | 0.483 mole H |
| Total Alkali Metal Hydroxide Used | | 0.483 mole |

The preferred solvent used in the reaction is 2-propanol. Other solvents that may be used include methanol, ethanol, 2-butanol, 1-butanol, t-butyl alcohol, 1-pentanol, 1-hexanol and 2-ethylhexanol. The amount of solvent should be sufficient to dissolve the starting material and solubilize the sulfurized product.

The hindered phenol mixture, elemental sulfur, alkali metal hydroxide, and solvent are combined at room temperature and slowly warmed to reflux temperature. The reaction is carried out at reflux for 30 minutes to 3 hours.

cation. In general, the crankcase oil is a formulated crankcase oil which is composed of between 75 and 90 wt. % of a lubrication base oil, between 0 and 10 wt. % of a polymeric viscosity index improver, and between 8 and 15 wt. % of an additive package. The additive package generally contains the following components:

Dispersants: The dispersants typically are nonmetallic additives containing nitrogen or oxygen polar groups attached to a high molecular weight hydrocarbon chain. The hydrocarbon chain provides solubility in the hydrocarbon base stocks. The dispersants function to keep oil degradation products suspended in the oil. Examples of commonly used dispersants include copolymers such as polymethacrylates and styrenemaleinic ester copolymers, substituted succinamides, polyamine succinamides, polyhydroxy succinic esters, substituted mannich bases, and substituted triazoles. Generally, the dispersant may be present in the finished oil between 4.0 and 8.5 wt %.

Detergents: The detergents typically are metallic additives containing charged polar groups, such as sulfonates or carboxylates, with aliphatic, cycloaliphatic, or alkylaromatic chains, and several metal ions. The detergents function by lifting deposits from the various surfaces of the engine. Examples of commonly used detergents include neutral and overbased alkali and alkaline earth metal sulfonates, neutral and overbased alkali and alkaline earth metal phenates, sulfurized phenates, overbased alkaline earth salicylates, phosphonates, thiopyrophosphonate, and thiophosphonates. Generally, the detergents may be present in the finished oil between 1.0 and 2.5 wt % by weight.

ZDDP's: The ZDDP's (zinc dihydrocarbyl dithiophosphates) typically are the most commonly used antiwear additives in formulated lubricants. These additives function by reacting with the metal surface to form a new surface active compound which itself is deformed and thus protects the original engine surface. Other examples of anti-wear additives include tricresyl phosphate, dilauryl phosphate, sulfurized terpenes and sulfurized fats. The ZDDP's also function as antioxidants. Generally, the ZDDP present in the finished oil contributes 600 to 1500 ppm of phosphorus. It is desirable from environmental concerns to have lower levels of ZDDP.

Antioxidants: Supplemental antioxidants, in addition to the sulfurized hindered phenols of this invention, may be used in oils that are less oxidatively stable or in oils that are subjected to unusually severe conditions. The supplementary antioxidants that are generally used include hindered phenols, hindered bisphenols, sulfurized phenols, alkylated diphenylamines, sulfurized olefins, alkyl sulfides and disulfides, dialkyl dithiocarbamates, phenothiazines, molybdenum compounds and copper salts. The inclusion of the sulfurized hindered phenols of this invention may eliminate the need for some of these supplementary antioxidants.

The lubrication oil component of this invention may be selected from any of the synthetic or natural oils used as lubricants such as that for crankcase lubrication oils for spark-ignited and compression-ignited internal combustion engines, e.g. automobile and truck engines, marine and railroad diesel engines. Synthetic base oils may include alkyl esters of dicarboxylic acids, polyglycols and alcohols, poly-alpha-olefins, including polybutenes, alkyl benzenes, organic esters of phosphoric acids, and polysilicone oils.

Natural base oils include mineral lubrication oils which may vary widely as to their crude source, e.g. as to whether they are paraffinic, naphthenic, or mixed paraffinic-naphthenic.

The lubrication oil base stock conveniently typically will have a viscosity of about 2.5 to about 15 cSt, and preferably about 2.5 to about 11 cSt, at 100° C.

The optional polymeric viscosity index improver (VII) component of this invention may be selected from any of the known viscosity index improvers. The function of the VII is to reduce the rate of change of viscosity with temperature, i.e. they cause minimal increase in engine oil viscosity at low temperature but considerable increase at high temperature. Examples of viscosity index improvers include polyisobutylenes, polymethacrylates, ethylene/propylene copolymers, polyacrylates, styrene/maleic ester copolymers, and hydrogenated styrene/butadiene copolymers.

In addition to the lubricant additives mentioned thus far, there is sometimes a need for other supplemental additives that perform specific functions not provided by the main components. These additional additives include, pour point depressants, corrosion inhibitors, rust inhibitors, foam inhibitors, and supplemental friction modifiers. Again, these additives are not always required but may be used in specific formulations that require them.

There are a number of recent trends in the petroleum additive industry that may restrict and/or limit the use of certain additives in formulated crankcase oils. The key trends are the move to lower phosphorus levels in the oils, the new fuel economy requirements and the move to more severe engine test conditions for qualifying oils. Such changes may show that certain currently used antioxidant additives are no longer effective in protecting the oil against oxidation. The sulfurized hindered phenols disclosed provide a solution to this need. Furthermore, there is concern that phosphorus from the lubricant tends to poison catalyst used in catalytic converters, thereby preventing them from functioning to full effect.

The following Examples show formulations for antioxidant additives in accordance with the present invention, and data from engine tests using lubricant oils containing the additive:

Example I

Sequence IIIE Evaluation of Sulfurized tert-Butylphenols

A series of lubrication formulations in accordance with this invention were tested in the Sequence IIIE engine test. The test uses a 231 CID (3.8 liter) Buick V-6 engine at high speed (3,000 rpm) and a very high oil temperature of 149 degrees C. for 64 hours. This test is used to evaluate an engine oil's ability to minimize oxidation, thickening, sludge, varnish, deposits, and wear. The formulations contained 7.6 wt. % viscosity index improver; 4.5 wt. % ashless dispersant; 1.0 wt. % ZDDP, i.e. low phosphorus; 1.6 wt. % detergents; 0.3 wt. % diphenylamine antioxidant; 0.5 wt. % supplemental additives; with the remainder being a hydrotreated mineral oil. The antioxidant additions, oil properties, and Sequence IIIE engine test results are shown in the table below.

| Formulation | Units | A | B | C |
|---|---|---|---|---|
| Sulfurized Phenols From Example II | Wt. % | 1.0 | 0 | 0 |
| Sulfurized Olefin | Wt. % | 0 | 0.7 | 0 |
| Dithiocarbamate | Wt. % | 0 | 0 | 0.5 |
| Oil Grade | SAE | 5W-30 | 5W-30 | 5W-30 |
| Phosphorus | ppm | 813 | 818 | 794 |
| Sulfur From Antioxidant | Wt. % | 0.10 | 0.14 | 0.15 |
| IIIE Test Results | Passing Limits | | | |
| % Vis Inc @ 64 h | 375 Max. | 17 | 3,576 | 3,358 |
| Hrs To 375% Visc Inc | 64 Min. | 83.5 | 52.9 | 56 |
| AE Sludge | 9.2 Min. | 9.7 | 9.3 | 9.3 |
| APS Varnish | 8.9 Min. | 9 | 8.6 | 8.4 |
| ORL Deposit | 3.5 Min. | 7 | 2.9 | 3 |
| Stuck Ring | | 0 | 0 | 0 |

|  | A | B | C |
|---|---|---|---|
| AC Wear | 30 Max. | 8.7 | 10.5 | 9.5 |
| MC Wear | 64 Max. | 12 | 13 | 13 |
| Oil Consumption | 5.1 Max. | 2.8 | 3.9 | 3.6 |

The sulfurized olefin and dithiocarbamate additives used in the comparative Example above represent conventional antioxidants that are commonly used in lubricants. The sulfurized olefin in this Example contains 20 wt. % sulfur. The dithiocarbamate in this Example contains 30.3 wt. % sulfur. The sulfurized t-butyl phenols of this invention contain 10.3 wt. % sulfur. One notes the excellent performance of the sulfurized t-butyl phenols in the Sequence IIIE test as compared to the conventional antioxidants even though the sulfur levels in the conventionally formulated oils is higher.

Example II

Sulfurization of tert-Butylphenols

A hindered phenolic antioxidant mixture composed of approximately 75 wt. % 2,6-di-t-butylphenol, 13 wt. % 2,4,6-tri-t-butylphenol, and 10 wt. % 2-t-butylphenol, was charged to a 3-liter, 3-neck round bottomed flask equipped with a mechanical stirrer, thermometer, heating mantle, and water cooled reflux condenser. To the phenolic mixture was added 2-propanol (600 g), elemental sulfur (264 g), and sodium hydroxide (120 g). The mixture was stirred under a dry nitrogen atmosphere while heating to the reflux temperature of 85° C. The reaction was held at reflux for 1 hour. A Dean-Stark trap was connected to the reactor to collect the 2-propanol while the reaction temperature was increased to 100° C. After collecting the majority of the 2-propanol a vacuum was applied to the reaction to remove the remaining 2-propanol. Water (600 g) was added and the mixture stirred for 30 minutes at 60° C. The bottom aqueous layer was removed and the organic layer dissolved in hexane (350 g). The reaction product was then washed with water (2×600 g) followed by very dilute $H_2SO_4$ (0.2 g acid in 600 g water). Hexane was removed under vacuum. An additional 500 g of hexane was added to the product, the solution filtered to remove residual insolubles, and the hexane removed under vacuum. This gave 640 g of a thick yellow oil. Analysis of the product showed the presence of 10.4 wt. % sulfur. HPLC analysis of the product showed the presence of the following components: 2-tert-butylphenol, 4.2 wt. %; 2,6-di-tert-butylphenol, 14.4 wt. %; 2,4,6-tri-tert-butylphenol, 7.3 wt. %; 4,4'-thiobis(2,6-di-tert-butylphenol), 23.0 wt. %; 4,4'-dithiobis(2,6-di-tert-butylphenol), 9.0 wt. %; 4,4'-trithiobis(2,6-di-tert-butylphenol), 13.4 wt. %; 4,4'-tetrathiobis(2,6-di-tert-butylphenol,), 8.9% (estimate); 4,4'-pentathiobis(2,6-di-t-butylphenol), 2.9% (estimate); 4,4'-hexathiobis(2,6-di-tert-butylphenol, 1.0% (estimate). The remaining components are believed to be unidentified hindered phenolic and sulfurized hindered phenolic compounds.

Example III

Sulfurization of 2,6-Di-sec-butylphenol

A sample of 2,6-di-sec-butylphenol (103.2 g) was charged to a 500 mL, 3 neck round bottomed flask equipped with a mechanical stirrer, thermometer, heating mantle, and a Dean-Stark trap with water cooled reflux condenser. To the phenolic mixture was added 2-propanol (140 g), elemental sulfur (56.1 g), and sodium hydroxide (26.7 g). The mixture was stirred under a dry nitrogen atmosphere while heating to the reflux temperature. The reaction was held at reflux for 1.5 hour. The 2-propanol was collected via the Dean-Stark trap while the reaction temperature was increased to 100° C. After collecting the majority of the 2-propanol a vacuum was applied to the reaction to remove the remaining 2-propanol. Water (100 g) was added and the mixture stirred for 30 minutes at 60° C. Hexane (100 g) was added and the bottom aqueous layer was removed. The reaction product was then washed with water (2×100 g) followed by very dilute $H_2SO_4$ (0.04 g acid in 100 g water). The organic phase was dried ($MgSO_4$) and concentrated under vacuum at 65–85° C. for 6–7 hours. This gave 107.2 g of a thick yellow oil. Analysis of the product showed the presence of 11.7 wt. % sulfur.

Example IV

Evaluation of Sulfurized tert-Butylphenols with Conventional Antioxidants

A sample of sulfurized tert-Butylphenols (sample prepared in Example II) and a variety of conventional hindered phenolic antioxidants were blended into an SAE grade 5W-30 type motor oil as shown in the table below. The only additional antioxidants in these blends were the zinc dialkyldithiophosphate (1.0 wt. % treat level) and alkylated diphenylamine Naugalube 680 (0.3 wt. % treat level). The oxidation stability of these oils was measured by pressurized differential scanning calorimetry (PDSC) as described by J. A. Walker and W. Tsang in "Characterization of Lubrication Oils by Differential Scanning Calorimetry", SAE Technical Paper Series, 801383 (Oct. 20–23, 1980). Oil samples were treated with an iron (III) naphthenate catalyst (approximately 55 ppm Fe) and 2.00 mg were analyzed in an open aluminum hermetic pan. The DSC cell was pressurized with 400 psi of an air/nitrogen dioxide mixture and programmed with the following heating sequence: (1) Jump to 140° C., (2) Ramp 10° C./min to 160° C., (3) Ramp 2° C./min to 170° C., (4) Isothermal at 170° C. The oil samples were held at 170° C. until an exothermic release of heat was observed. The exothermic release of heat marks the oxidation reaction. The time from the start of the experiment to the exothermic release of heat is called the oxidation induction time and is a measure of the oxidative stability of the oil (i.e. the longer the oxidation induction time the greater the oxidative stability of the oil).

| Oil Sample | Antioxidant | Conc. (Wt. %) Of Antioxidant | Number of PDSC Runs | Mean OIT (min) |
|---|---|---|---|---|
| 1 | none | 0.0 | 3 | 35.4 |
| 2 | H-4702 | 1.0 | 2 | 60.9 |
| 3 | H-4728 | 1.0 | 2 | 56.8 |
| 4 | L-118 | 1.0 | 2 | 59.3 |
| 5 | L-134 | 1.0 | 2 | 56.2 |
| 6 | L-135 | 1.0 | 3 | 50.4 |
| 7 | N-531 | 1.0 | 5 | 57.8 |
| 8 | N-431 | 1.0 | 4 | 55.9 |
| 9 | Sulfurized Phenols From Example II | 1.0 | 5 | 71.3 |

HiTEC® 4702 is methylenebis(2,6-di-t-butylphenol) available from Ethyl Corporation; HiTEC® 4728 is methylene-bridged polyalkyphenols available from Ethyl Corporation; L-118 is [[[3,5-Bis(1,1-dimethylethyl)-4-hydroxyphenyl)methyl]thio]acetic acid, C10–C14-isoalkyl esters available from Ciba-Geigy Corporation; L-134 is 2,6-di-t-butylphenol and Isooctyl 3,5-di-t-butyl-4-hydroxyhydrocinnamate mixture available from Ciba-Geigy Corporation; L-135 is Isooctyl 3,5-di-t-butyl-4-hydroxyhydrocinnamate available from Ciba-Geigy Corporation; N-531 is 3,5-di-t-butyl-4-hydroxyhydrocinnamic acid, C7–C9 branched alkyl ester available from Uniroyal Chemical Company; N-431 is Alkylated p-cresol available from Uniroyal Chemical Company.

The results clearly show that the sulfurized t-butylphenols from Example II, oil sample #9 above, provide superior oxidation protection to the formulated oil. Other classes of hindered phenols, oils #2 through #8, are not as effective at equal concentrations.

Example V

D-130 Copper Corrosion Testing of Sulfurized tert-Butylphenols

Lubricant compositions of a fully formulated 5W-30 crankcase lubricant oil (formulations A through C in Example I) were tested in the D-130 Copper Corrosion Test at 121° C. for 3 hours.

This test indicates the resistance of the lubricant to corrosion of copper. A freshly refinished copper strip is placed in a 1×6 in. (25.4×152.4 mm) test tube with 25 g of the oil being tested. The tube is placed in a heating bath for the proper period of time. After removal from the bath, the condition of the strip is compared with a set of standard strips and given a rating according to the standard strip most closely matched. The ratings ranged from 1 to 4 with the letter a to d for intermediate ranges.

The rating for formulation A in Example I was 1a, indicating a very low level of copper corrosion in this test.

Example VI

Preparation of Sulfurized Hindered Phenols

Sulfurized hindered phenols were prepared as described in example II with the modifications outlined in Table I below:

TABLE I

| Sample | t-Butyl-phenols (g) | 2,6-DSBP (g) | Sulfur (g) | NaOH (g) | 2-propanol (g) | Reaction Time (h) |
|---|---|---|---|---|---|---|
| A | 620.4 | 0 | 264.0 | 120.0 | 600.0 | 1.25 |
| B | 620.4 | 0 | 237.6 | 120.0 | 600.0 | 3.25 |
| C | 569.1 | 51.2 | 264.0 | 120.0 | 600.0 | 3.25 |
| D | 569.1 | 51.2 | 237.6 | 120.0 | 600.0 | 1.25 |

2,6-DSBP is 2,6-di-sec-butylphenol, commercially available from Schenectady, Int.

The isolated products were analyzed for sulfur content, visual appearance, and solubility at room temperature, 50° C., and 60° C. in 50 weight % Exxon FN1305 Pail Parafin Oil. The results are in Table II below:

TABLE II

| Sample | sulfur content (wt. %) | Appearance After 1 month | solubility, room temperature | solubility, 50° C. | solubility, 60° C. |
|---|---|---|---|---|---|
| A | 10.53 | trace crystallization | soluble | soluble | soluble |
| B | 8.34 | heavy crystallization | crystallization | crystallization | soluble |
| C | 10.34 | completely liquid | soluble | soluble | soluble |
| D | 8.29 | some crystallization | crystallization | soluble | soluble |

Appearance of 100% active material after one month standing at room temperature.
Solubility determined in 50 weight % Exxon FN1305 Pail Parafin Oil This Example shows that samples prepared with a lower sulfur content are generally more crystalline and less oil soluble than samples prepared with a high sulfur content. However, all samples within the sulfur range studied were soluble in 50% oil at 60° C. This is in contrast to the pure $S_1$, $S_2$, and $S_3$ compounds which all have melting point above 100° C.

In view of the foregoing description of the present invention, it will be within the ability of one skilled in the art to make modifications to the present invention, such as through the substitution of equivalent components and/or process steps, so as to be able to practice the invention without departing from its spirit as reflected in the appended claims.

What is claimed is:

1. An antioxidant composition comprising at least one thiophenol, wherein said antioxidant composition is prepared by a process comprising
   (a) preparing a mixture of:
      (i) at least two different chlorine-free reactive hindered phenols, wherein said reactive hindered phenols comprise a mixture of at least one dialkyl substituted phenol and at least one monoalkyl substituted phenol;
      (ii) a chlorine-free sulfur source; and
      (iii) at least one alkali metal hydroxide promoter;
      in a polar solvent; and
   (b) causing components (i), (ii) and (iii) to react for sufficient time and at sufficient temperature so as to form an antioxidant composition, said antioxidant composition being substantially free of chlorine, and said antioxidant composition being in a substantially liquid form.

2. The antioxidant composition according to claim 1 wherein said alkyl groups of the monoalkyl- and dialkyl-substituted phenols are independently alkyl groups of 3 to 12 carbons.

3. The antioxidant composition according to claim 2 wherein said alkyl groups of the monoalkyl- and dialkyl-substituted phenols are independently alkyl groups of 4 to 6 carbons.

4. A lubricating composition comprising the antioxidant composition according to claim 1.

5. The lubricating composition according to claim 4 wherein said antioxidant composition is present in said lubricating composition at a concentration in the range of from 0.005% to about 5.0% by weight.

6. The lubricating composition according to claim 5 wherein said antioxidant composition is present in said lubricating composition at a concentration in the range of from 0.05% to about 2.0% by weight.

7. The lubricating composition according to claim 4, said lubricating composition additionally comprising at least one composition selected from the group consisting of dispersants, detergents, antiwear additives, supplemental antioxidants, viscosity index improvers, pour point depressants, corrosion inhibitors, rust inhibitors, foam inhibitors; and supplemental friction modifiers.

8. The lubricating composition according to claim 7, wherein said supplemental antioxidants are selected from the group consisting of diphenylamines, alkylated diphenylamines, phenyl-napthylamines, tert-butylphenols, sulfurized alkylphenols, sulfurized olefins, dithiocarbamates, oil soluble copper compounds, and oil soluble molybdenum compounds.

9. An additive composition comprising:
  A) from about 30% to about 95% by weight of an antioxidant composition prepared by a process comprising
    (a) preparing a mixture of:
      (i) at least two different chlorine-free reactive hindered phenols, wherein said reactive hindered phenols comprise a mixture of at least one dialkyl substituted phenol and at least one monoalkyl substituted phenol;
      (ii) a chlorine-free sulfur source; and
      (iii) at least one alkali metal hydroxide promoter; in a polar solvent; and
    (b) causing components (i), (ii) and (iii) to react for sufficient time and at sufficient temperature so as to form an antioxidant composition, said antioxidant composition being substantially free of chlorine, and said antioxidant composition being in a substantially liquid form; and
  B) the balance of said additive composition comprising at least one mineral or synthetic lubricant oil.

10. The additive composition according to claim 9 wherein said alkyl groups of the monoalkyl- and dialkyl-substituted phenols are independently alkyl groups of 3 to 12 carbons.

11. The additive composition according to claim 10 wherein said alkyl groups of the monoalkyl- and dialkyl-substituted phenols are independently alkyl groups of 4 to 6 carbons.

12. A method of reducing the oxidative environment in a petroleum composition selected from the group consisting of lubricating compositions and liquid organic fuels, said method comprising adding to said petroleum composition an effective amount of an antioxidant composition wherein said antioxidant composition is prepared by a process comprising
  (a) preparing a mixture of:
    (i) at least two different chlorine-free reactive hindered phenols, wherein said reactive hindered phenols comprise a mixture of at least one dialkyl substituted phenol and at least one monoalkyl substituted phenol;
    (ii) a chlorine-free sulfur source; and
    (iii) at least one alkali metal hydroxide promoter; in a polar solvent; and
  (b) causing components (i), (ii) and (iii) to react for sufficient time and at sufficient temperature so as to form an antioxidant composition, said antioxidant composition being substantially free of chlorine, and said antioxidant composition being in a substantially liquid form.

13. The method according to claim 12 wherein said alkyl groups of the monoallyl- and dialkyl-substituted phenols are independently alkyl groups of 3 to 12 carbons.

14. The method according to claim 13 wherein said alkyl groups of the monoalkyl- and diallyl-substituted phenols are independently alkyl groups of 4 to 6 carbons.

15. A method according to claim 12 wherein said antioxidant composition is present in said petroleum composition at a concentration in the range of from 0.05% to about 5.0% by weight.

16. A method according to claim 15 wherein said antioxidant composition is present in said petroleum composition at a concentration in the range of from 0.5% to about 2.0% by weight.

* * * * *

UNITED STATES PATENT AND TRADEMARK OFFICE
CERTIFICATE OF CORRECTION

PATENT NO. : 6,096,695
DATED : 8-1-00
INVENTOR(S) : William Y. Lam and Vincent J. Gatto It is certified that error appears in the above-indentified patent and that said Letters Patent is hereby corrected as shown below:

Column 7, line 13 - change "2,4,64" to "2,4,6";
Column 13, line 1 - change "L-1 18" to "L-118";
Column 16, line 26 - change "monoallyl" to "monoalkyl"; and
Column 16, line 29 - change "diallyl" to "dialkyl".

Signed and Sealed this

Tenth Day of April, 2001

Attest:

NICHOLAS P. GODICI

Attesting Officer

Acting Director of the United States Patent and Trademark Office